United States Patent
Farwick et al.

(10) Patent No.: US 7,026,158 B2
(45) Date of Patent: Apr. 11, 2006

(54) NUCLEOTIDE SEQUENCES WHICH CODE FOR THE MIKE17 GENE

(75) Inventors: Mike Farwick, Bielefeld (DE); Klaus Huthmacher, Gelnhausen (DE); Walter Pfefferle, Halle (DE)

(73) Assignee: Degussa AG, Dusseldorf (DE)

( * ) Notice: Subject to any disclaimer, the term of this patent is extended or adjusted under 35 U.S.C. 154(b) by 632 days.

(21) Appl. No.: 09/825,293

(22) Filed: Apr. 4, 2001

(65) Prior Publication Data

US 2002/0106749 A1 Aug. 8, 2002

(30) Foreign Application Priority Data

Sep. 27, 2000 (DE) .......................... 100 47 867
Mar. 22, 2001 (DE) .......................... 101 13 958

(51) Int. Cl.
*C12N 1/20* (2006.01)

(52) U.S. Cl. .............. 435/252.3; 435/69.1; 435/252.32; 435/320.1; 530/350; 536/23.2

(58) Field of Classification Search ................. 435/69.1, 435/252.3, 252.32, 320.1; 530/350; 536/23.2
See application file for complete search history.

(56) References Cited

FOREIGN PATENT DOCUMENTS

| EP | 0 387 527 | 8/1990 |
|---|---|---|
| EP | 1 108 790 | 6/2001 |
| EP | 1 106 693 | 8/2001 |
| WO | WO 01 00843 | 1/2001 |

OTHER PUBLICATIONS

Mahairas et al. Accession AQ757887. Jul. 27, 1999 (Alignment No. 1).*
Lee et al. Accession BE636602. Aug. 25, 2000 (Alignment No. 2).*
Schauwecker et al. Accession AAF25795. Dec. 21, 2000.*
Attwood et al. Which craft is best in bioinformatics? Comput. Chem. 2001, vol. 25(4), pp.329□339.*
Ponting, C.P. Issues in predicting protein function from sequence. Brief. Bioinform. Mar. 2001, vol. 2(1), pp. 19□29.*
Reeves et al. Accession AAA14663. Aug. 8, 2000.*
Murdin et al. Accession AAZ61503. Jun. 19, 2000.*
Cole, et al., "Decipharing the biology of Mycobacterium tuberculosis from the complete genome sequence," Nature, vol. 393, 1998, p. 537–544.
Radenbach, et al., "A set of ordered cosmids and a detailed genetic and physical map for the 8 mb streptomyces coell-color A3(2) chromosome," Molecular Microbiology, vol. 21, No. 1, 1995, p. 77–96.
Kramer, et al., "Genetic and physiological approaches for the production of amino acids," Journal of Biotechnology, vol. 45, No. 1, 1996, p. 1–21.
Eikmanns, et al., "Molecular aspects of lysine, threonine and isoleucine biosynthesis in *Corynabacterium glutamicum*," Antonie Van Lesuwenhoek, vol. 64, No. 2, 1993, p. 145–163.
Vifjic, et al., "A new type of trasnport with a new type of cellular function: L–lyaine export from *Corynebacterium glutamicum*," Molecular Microbiology, vol. 22, No. 5, 1986, p. 815–826.
English language abstract of IR above.

\* cited by examiner

*Primary Examiner*—Ponnathapu Achutamurthy
*Assistant Examiner*—Christian L Fronda
(74) *Attorney, Agent, or Firm*—Pillsbury Winthrop LLP

(57) ABSTRACT

The invention relates to an isolated polynucleotide comprising a polynucleotide sequence chosen from the group consisting of a) polynucleotide which is identical to the extent of at least 70% to a polynucleotide which codes for a polypeptide which comprises the amino acid sequence of SEQ ID No. 2,
b) polynucleotide which codes for a polypeptide which comprises an amino acid sequence which is identical to the extent of at least 70% to the amino acid sequence of SEQ ID No. 2,
c) polynucleotide which is complementary to the polynucleotides of a) or b), and
d) polynucleotide comprising at least 15 successive nucleotides of the polynucleotide sequence of a), b) or c), and a process for the fermentative preparation of L-amino acids using coryneform bacteria in which at least the mikE17 gene is present in attenuated form, and the use of polynucleotides which comprise the sequences according to the invention as hybridization probes.

16 Claims, 1 Drawing Sheet

SEQUENCE LISTING

<160> NUMBER OF SEQ ID NOS: 4

<210> SEQ ID NO 1
<211> LENGTH: 1890
<212> TYPE: DNA
<213> ORGANISM: Corynebacterium glutamicum
<220> FEATURE:
<221> NAME/KEY: CDS
<222> LOCATION: (252)..(1673)
<223> OTHER INFORMATION: mikE17-Gen

<400> SEQUENCE: 1

```
aaccccgttt ggtatcaacc aaaaagttta gacagcccaa ccttccgatc cagggagcaa      60
ctttgcgcag gtgacacaat tatcccaaca gttgcaccgt aggtgcctaa aaagttcccg     120
gggcggatgt ggcccgacca cgccgggcac ctggtggcgg cgggctgcgt cgaaaagcga     180
aaatcaacaa gtttgcaaca cctcagtgcc aagagtggtt aaggtgatgg tgatcacgct     240
atagttgcgc c atg gga aag aca tat gtg ggg tcc agg ctg cgc caa ctg      290
          Met Gly Lys Thr Tyr Val Gly Ser Arg Leu Arg Gln Leu
            1               5                  10 cgc cgc gaa aga gac ctg agc cag gca tcc tta gca gca acc ctt ggc      338
Arg Arg Glu Arg Asp Leu Ser Gln Ala Ser Leu Ala Ala Thr Leu Gly
 15                  20                  25 tta tct gca agt tat gta aat cag att gag cac gac gta cgc ccg ctc      386
Leu Ser Ala Ser Tyr Val Asn Gln Ile Glu His Asp Val Arg Pro Leu
 30                  35                  40                  45 acc gta ccg gtg tta ttg cgc atc acc gag gcg ttc ggc gta gac gca      434
Thr Val Pro Val Leu Leu Arg Ile Thr Glu Ala Phe Gly Val Asp Ala
                 50                  55                  60
```

```
acg ttt ttc tcc cgc gac gat gac tcc cgc ctg ctc gcc gag gtc caa      482
Thr Phe Phe Ser Arg Asp Asp Asp Ser Arg Leu Leu Ala Glu Val Gln
            65                  70                  75 gac gtc atg ctg gac cgg gag atc aat cct gcg aac gtg gag ctg caa      530
Asp Val Met Leu Asp Arg Glu Ile Asn Pro Ala Asn Val Glu Leu Gln
        80                  85                  90 gag ctt tcg gag atg gtg tac aac cac ccc caa cta gcg cgc gcg atg      578
Glu Leu Ser Glu Met Val Tyr Asn His Pro Gln Leu Ala Arg Ala Met
    95                  100                 105 gtg gaa atg cac cag cgt tac cga aac gtg cgc gat aag ttc tcc atc      626
Val Glu Met His Gln Arg Tyr Arg Asn Val Arg Asp Lys Phe Ser Ile
110                 115                 120                 125 gca gtg gat aat cgc acc aac acg cct gag gaa cgc cgt ccc atc gcg      674
Ala Val Asp Asn Arg Thr Asn Thr Pro Glu Glu Arg Arg Pro Ile Ala
            130                 135                 140 gag gcc gtg agc atg ccg cac gaa gag gtc cgc gat ttc att tac gcc      722
Glu Ala Val Ser Met Pro His Glu Glu Val Arg Asp Phe Ile Tyr Ala
        145                 150                 155 cgc caa aac tac ttc gat gcc ctt gac cgc cgc gcc gaa gcc atc gcc      770
Arg Gln Asn Tyr Phe Asp Ala Leu Asp Arg Arg Ala Glu Ala Ile Ala
    160                 165                 170 gcg caa ctg ggc tgg cag ccg tac gat tcc cgc gcc atg gaa gat tcg      818
Ala Gln Leu Gly Trp Gln Pro Tyr Asp Ser Arg Ala Met Glu Asp Ser
175                 180                 185 atc gcc cgc cgc ctg caa atg gat cac gat gtc acc atc acc tcc tcc      866
Ile Ala Arg Arg Leu Gln Met Asp His Asp Val Thr Ile Thr Ser Ser
190                 195                 200                 205 aaa gag gaa tcc ggc acg ctg cac cac ttc gac ccc gag acg cgt ctg      914
Lys Glu Glu Ser Gly Thr Leu His His Phe Asp Pro Glu Thr Arg Leu
            210                 215                 220 ctg aca atc cac gca cgc ctc aac ccc ggg caa cgc gcc ttc cgc atg      962
Leu Thr Ile His Ala Arg Leu Asn Pro Gly Gln Arg Ala Phe Arg Met
        225                 230                 235 gcc acc gaa ctc ggc tac cta gaa gcc aac gac ctc atc gaa ggt atc     1010
Ala Thr Glu Leu Gly Tyr Leu Glu Ala Asn Asp Leu Ile Glu Gly Ile
    240                 245                 250 gtt gac gac ggc atc tgg tcc acc ccc gaa gcc cgc acc cta gcc atc     1058
Val Asp Asp Gly Ile Trp Ser Thr Pro Glu Ala Arg Thr Leu Ala Ile
255                 260                 265 cgc ggt gtg gcc tcc tac ttc gcc gcc gcc gtg atg ctg ccc tac aaa     1106
Arg Gly Val Ala Ser Tyr Phe Ala Ala Ala Val Met Leu Pro Tyr Lys
270                 275                 280                 285 atc ttc cac tcc gag gcc gaa aaa tcc ggc tac gac atc gag tac cta     1154
Ile Phe His Ser Glu Ala Glu Lys Ser Gly Tyr Asp Ile Glu Tyr Leu
            290                 295                 300 ggc caa ctc ttt ggc gtg ggc tat gag aca acc gcc cac cgc ttg tcc     1202
Gly Gln Leu Phe Gly Val Gly Tyr Glu Thr Thr Ala His Arg Leu Ser
        305                 310                 315 acc ctg cag cgc ccc aac ctg cgc ggc atc ccc ttt acc ttc gtg cgc     1250
Thr Leu Gln Arg Pro Asn Leu Arg Gly Ile Pro Phe Thr Phe Val Arg
    320                 325                 330 gtc gac cgc gcc ggc aac atg tcc aaa cgc caa tcc gcc acc ggc ttc     1298
Val Asp Arg Ala Gly Asn Met Ser Lys Arg Gln Ser Ala Thr Gly Phe
335                 340                 345 cac ttc acc cac tac ggc ggc acc tgc ccc ctg tgg aac gtg ttt gaa     1346
His Phe Thr His Tyr Gly Gly Thr Cys Pro Leu Trp Asn Val Phe Glu
350                 355                 360                 365 acc ttc acc aac ccc ggc caa gtg ctc cgc caa ttc gcg caa atg ccc     1394
Thr Phe Thr Asn Pro Gly Gln Val Leu Arg Gln Phe Ala Gln Met Pro
```

-continued

```
                    370                 375                 380
gac gga cgc aac tac ctg tgg atc tca cgc acc gtg cga cac cac gaa    1442
Asp Gly Arg Asn Tyr Leu Trp Ile Ser Arg Thr Val Arg His His Glu
                385                 390                 395 gcc cgg ttc ggc gaa gta gac aaa atg ttc gcc atc ggc ctg ggc tgc    1490
Ala Arg Phe Gly Glu Val Asp Lys Met Phe Ala Ile Gly Leu Gly Cys
            400                 405                 410 gaa gcg cgc cac gcc gac cgc act gtg tac tcc cgc ggt ttc aac ctc    1538
Glu Ala Arg His Ala Asp Arg Thr Val Tyr Ser Arg Gly Phe Asn Leu
        415                 420                 425 cag gac ctc tcc acc gcc acc ccc atc ggg tcc ggc tgc cga gtg tgc    1586
Gln Asp Leu Ser Thr Ala Thr Pro Ile Gly Ser Gly Cys Arg Val Cys
430                 435                 440                 445 acc cgc gag aac tgc gcg cag cgc gca ttc cca tcc gtc cac ggc cgc    1634
Thr Arg Glu Asn Cys Ala Gln Arg Ala Phe Pro Ser Val His Gly Arg
                450                 455                 460 atc aac atc gac gcg cac gaa tcc act atc gcg ccg tac taagaaaagg    1683
Ile Asn Ile Asp Ala His Glu Ser Thr Ile Ala Pro Tyr
            465                 470 agcttgcttt acgacgcacc ctgcgggggt gggttttacc ttttatgaat gatcagcaat    1743
atccgcgtaa acaccatcgg tagccagaag aacatcatcc ggggcgataa tcagggacca    1803
cccgcgtcgc cctgcgctga cgtagattcg ctcctggaga attgcagact catccaaaaa    1863
cacgcggtgc ttgttcttct gccctat                                        1890

<210> SEQ ID NO 2
<211> LENGTH: 474
<212> TYPE: PRT
<213> ORGANISM: Corynebacterium glutamicum

<400> SEQUENCE: 2

Met Gly Lys Thr Tyr Val Gly Ser Arg Leu Arg Gln Leu Arg Arg Glu
 1               5                  10                  15

Arg Asp Leu Ser Gln Ala Ser Leu Ala Ala Thr Leu Gly Leu Ser Ala
            20                  25                  30

Ser Tyr Val Asn Gln Ile Glu His Asp Val Arg Pro Leu Thr Val Pro
        35                  40                  45

Val Leu Leu Arg Ile Thr Glu Ala Phe Gly Val Asp Ala Thr Phe Phe
    50                  55                  60

Ser Arg Asp Asp Ser Arg Leu Leu Ala Glu Val Gln Asp Val Met
65                  70                  75                  80

Leu Asp Arg Glu Ile Asn Pro Ala Asn Val Glu Leu Gln Glu Leu Ser
                85                  90                  95

Glu Met Val Tyr Asn His Pro Gln Leu Ala Arg Ala Met Val Glu Met
            100                 105                 110

His Gln Arg Tyr Arg Asn Val Arg Asp Lys Phe Ser Ile Ala Val Asp
        115                 120                 125

Asn Arg Thr Asn Thr Pro Glu Glu Arg Arg Pro Ile Ala Glu Ala Val
    130                 135                 140

Ser Met Pro His Glu Glu Val Arg Asp Phe Ile Tyr Ala Arg Gln Asn
145                 150                 155                 160

Tyr Phe Asp Ala Leu Asp Arg Arg Ala Glu Ala Ile Ala Ala Gln Leu
                165                 170                 175

Gly Trp Gln Pro Tyr Asp Ser Arg Ala Met Glu Asp Ser Ile Ala Arg
            180                 185                 190

Arg Leu Gln Met Asp His Asp Val Thr Ile Thr Ser Ser Lys Glu Glu
```

```
                195                 200                 205
Ser Gly Thr Leu His His Phe Asp Pro Glu Thr Arg Leu Leu Thr Ile
    210                 215                 220

His Ala Arg Leu Asn Pro Gly Gln Arg Ala Phe Arg Met Ala Thr Glu
225                 230                 235                 240

Leu Gly Tyr Leu Glu Ala Asn Asp Leu Ile Glu Gly Ile Val Asp Asp
                245                 250                 255

Gly Ile Trp Ser Thr Pro Glu Ala Arg Thr Leu Ala Ile Arg Gly Val
            260                 265                 270

Ala Ser Tyr Phe Ala Ala Val Met Leu Pro Tyr Lys Ile Phe His
        275                 280                 285

Ser Glu Ala Glu Lys Ser Gly Tyr Asp Ile Glu Tyr Leu Gly Gln Leu
    290                 295                 300

Phe Gly Val Gly Tyr Glu Thr Thr Ala His Arg Leu Ser Thr Leu Gln
305                 310                 315                 320

Arg Pro Asn Leu Arg Gly Ile Pro Phe Thr Phe Val Arg Val Asp Arg
                325                 330                 335

Ala Gly Asn Met Ser Lys Arg Gln Ser Ala Thr Gly Phe His Phe Thr
            340                 345                 350

His Tyr Gly Gly Thr Cys Pro Leu Trp Asn Val Phe Glu Thr Phe Thr
        355                 360                 365

Asn Pro Gly Gln Val Leu Arg Gln Phe Ala Gln Met Pro Asp Gly Arg
    370                 375                 380

Asn Tyr Leu Trp Ile Ser Arg Thr Val Arg His His Glu Ala Arg Phe
385                 390                 395                 400

Gly Glu Val Asp Lys Met Phe Ala Ile Gly Leu Gly Cys Glu Ala Arg
                405                 410                 415

His Ala Asp Arg Thr Val Tyr Ser Arg Gly Phe Asn Leu Gln Asp Leu
            420                 425                 430

Ser Thr Ala Thr Pro Ile Gly Ser Gly Cys Arg Val Cys Thr Arg Glu
        435                 440                 445

Asn Cys Ala Gln Arg Ala Phe Pro Ser Val His Gly Arg Ile Asn Ile
    450                 455                 460

Asp Ala His Glu Ser Thr Ile Ala Pro Tyr
465                 470

<210> SEQ ID NO 3
<211> LENGTH: 19
<212> TYPE: DNA
<213> ORGANISM: Corynebacterium glutamicum
<220> FEATURE:
<223> OTHER INFORMATION: Primer mikE17-int1

<400> SEQUENCE: 3
aatggatcac gatgtcacc                                              19

<210> SEQ ID NO 4
<211> LENGTH: 19
<212> TYPE: DNA
<213> ORGANISM: Corynebacterium glutamicum
<220> FEATURE:
<223> OTHER INFORMATION: Primer mikE17-int2

<400> SEQUENCE: 4
tagtgggtga agtggaagc                                              19
```

NUCLEOTIDE SEQUENCES WHICH CODE FOR THE MIKE17 GENE

CROSS REFERENCE TO RELATED APPLICATIONS

The present application claims priority under 35 U.S.C. §119 to German application 100 47 867.0, filed on Sep. 27, 2000 and German application 101 13 958.6, filed on Mar. 22, 2001.

FIELD OF THE INVENTION

The invention provides nucleotide sequences from coryneform bacteria which code for the mikE17 gene and a process for the fermentative preparation of amino acids using bacteria in which the mikE17 gene is attenuated.

PRIOR ART

L-Amino acids, in particular L-lysine, are used in human medicine and in the pharmaceuticals industry, in the foodstuffs industry and very particularly in animal nutrition.

It is known that amino acids are prepared by fermentation from strains of coryneform bacteria, in particular Corynebacterium glutamicum. Because of their great importance, work is constantly being undertaken to improve the preparation processes. Improvements to the process can relate to fermentation measures, such as, for example, stirring and supply of oxygen, or the composition of the nutrient media, such as, for example, the sugar concentration during the fermentation, or the working up to the product form by, for example, ion exchange chromatography, or the intrinsic output properties of the microorganism itself.

Methods of mutagenesis, selection and mutant selection are used to improve the output properties of these microorganisms. Strains which are resistant to antimetabolites or are auxotrophic for metabolites of regulatory importance and which produce amino acids are obtained in this manner.

Methods of the recombinant DNA technique have also been employed for some years for improving the strain of Corynebacterium strains which produce L-amino acid, by amplifying individual amino acid biosynthesis genes and investigating the effect on the amino acid production.

OBJECT OF THE INVENTION

The inventors had the object of providing new measures for improved fermentative preparation of amino acids.

DESCRIPTION OF THE INVENTION

Where L-amino acids or amino acids are mentioned in the following, this means one or more amino acids, including their salts, chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. L-Lysine is/are particularly preferred.

When L-lysine or lysine are mentioned in the following, not only the bases but also the salts, such as e.g. lysine monohydrochloride or lysine sulfate, are meant by this.

The invention provides an isolated polynucleotide from coryneform bacteria, comprising a polynucleotide sequence which codes for the mikE17 gene, chosen from the group consisting of a) polynucleotide which is identical to the extent of at least 70% to a polynucleotide which codes for a polypeptide which comprises the amino acid sequence of SEQ ID No. 2, b) polynucleotide which codes for a polypeptide which comprises an amino acid sequence which is identical to the extent of at least 70% to the amino acid sequence of SEQ ID No. 2, c) polynucleotide which is complementary to the polynucleotides of a) or b), and d) polynucleotide comprising at least 15 successive nucleotides of the polynucleotide sequence of a), b) or c), the polypeptide preferably having the activity of the transcription regulator MikE17.

The invention also provides the abovementioned polynucleotide, this preferably being a DNA which is capable of replication, comprising:

(i) the nucleotide sequence, shown in SEQ ID No.1, or (ii) at least one sequence which corresponds to sequence (i) within the range of the degeneration of the genetic code, or (iii) at least one sequence which hybridizes with the sequences complementary to sequences (i) or (ii), and optionally (iv) sense mutations of neutral function in (i).

The invention also provides:

a polynucleotide, in particular DNA, which is capable of replication and comprises the nucleotide sequence as shown in SEQ ID No.1;

a polynucleotide which codes for a polypeptide which comprises the amino acid sequence as shown in SEQ ID No. 2;

a vector containing parts of the polynucleotide according to the invention, but at least 15 successive nucleotides of the sequence claimed, and coryneform bacteria in which the mikE17 gene is attenuated, in particular by an insertion or deletion.

The invention also provides polynucleotides which substantially comprise a polynucleotide sequence, which are obtainable by screening by means of hybridization of a corresponding gene library of a coryneform bacterium, which comprises the complete gene or parts thereof, with a probe which comprises the sequence of the polynucleotide according to the invention according to SEQ ID No.1 or a fragment thereof, and isolation of the polynucleotide sequence mentioned.

Polynucleotides which comprise the sequences according to the invention are suitable as hybridization probes for RNA, cDNA and DNA, in order to isolate, in the full length, nucleic acids or polynucleotides or genes which code for the transcription regulator MikE17 or to isolate those nucleic acids or polynucleotides or genes which have a high similarity with the sequence of the mikE17 gene.

Polynucleotides which comprise the sequences according to the invention are furthermore suitable as primers with the aid of which DNA of genes which code for the transcription regulator MikE17 can be prepared by the polymerase chain reaction (PCR).

Such oligonucleotides which serve as probes or primers comprise at least 30, preferably at least 20, very particularly preferably at least 15 successive nucleotides. Oligonucleotides which have a length of at least 40 or 50 nucleotides are also suitable.

"Isolated" means separated out of its natural environment.

"Polynucleotide" in general relates to polyribonucleotides and polydeoxyribonucleotides, it being possible for these to be non-modified RNA or DNA or modified RNA or DNA.

The polynucleotides according to the invention include a polynucleotide according to SEQ ID No. 1 or a fragment prepared therefrom and also those which are at least 70%, preferably at least 80% and in particular at least 90% to 95% identical to the polynucleotide according to SEQ ID No. 1 or a fragment prepared therefrom.

"Polypeptides" are understood as meaning peptides or proteins which comprise two or more amino acids bonded via peptide bonds.

The polypeptides according to the invention include a polypeptide according to SEQ ID No. 2, in particular those with the biological activity of the transcription regulator MikE17, and also those which are at least 70%, preferably at least 80% and in particular at least 90% to 95% identical to the polypeptide according to SEQ ID No. 2 and have the activity mentioned.

The invention furthermore relates to a process for the fermentative preparation of amino acids chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine using coryneform bacteria which in particular already produce amino acids and in which the nucleotide sequences which code for the mikE17 gene are attenuated, in particular eliminated or expressed at a low level.

The term "attenuation" in this connection describes the reduction or elimination of the intracellular activity of one or more enzymes (proteins) in a microorganism which are coded by the corresponding DNA, for example by using a weak promoter or using a gene or allele which codes for a corresponding enzyme with a low activity or inactivates the corresponding gene or enzyme (protein), and optionally combining these measures.

The microorganisms to which the present invention relates can prepare amino acids from glucose, sucrose, lactose, fructose, maltose, molasses, starch, cellulose or from glycerol and ethanol. They can be representatives of coryneform bacteria, in particular of the genus *Corynebacterium*. Of the genus *Corynebacterium*, there may be mentioned in particular the species *Corynebacterium glutamicum*, which is known among experts for its ability to produce L-amino acids.

Suitable strains of the genus *Corynebacterium*, in particular of the species *Corynebacterium glutamicum* (*C. glutamicum*), are in particular the known wild-type strains

*Corynebacterium glutamicum* ATCC13032

*Corynebacterium acetoglutamicum* ATCC15806

*Corynebacterium acetoacidophilum* ATCC13870

*Corynebacterium melassecola* ATCC17965

*Corynebacterium thermoaminogenes* FERM BP-1539

*Brevibacterium flavum* ATCC14067

*Brevibacterium lactofermentum* ATCC13869 and

*Brevibacterium divaricatum* ATCC14020 and L-amino acid-producing mutants or strains prepared therefrom.

The new mikE17 gene from *C. glutamicum* which codes for the transcription regulator MikE17 has been isolated.

To isolate the mikE17 gene or also other genes of *C. glutamicum*, a gene library of this microorganism is first set up in *Escherichia coli* (*E. coli*). The setting up of gene libraries is described in generally known textbooks and handbooks. The textbook by Winnacker: Gene und Klone, Eine Einführung in die Gentechnologie [Genes and Clones, An Introduction to Genetic Engineering] (Verlag Chemie, Weinheim, Germany, 1990), or the handbook by Sambrook et al.: Molecular Cloning, A Laboratory Manual (Cold Spring Harbor Laboratory Press, 1989) may be mentioned as an example. A well-known gene library is that of the *E. coli* K-12 strain W3110 set up in λ vectors by Kohara et al. (Cell 50, 495–508 (1987)). Bathe et al. (Molecular and General Genetics, 252:255–265, 1996) describe a gene library of *C. glutamicum* ATCC13032, which was set up with the aid of the cosmid vector SuperCos I (Wahl et al., 1987, Proceedings of the National Academy of Sciences USA, 84:2160–2164) in the *E. coli* K-12 strain NM554 (Raleigh et al., 1988, Nucleic Acids Research 16:1563–1575).

Börmann et al. (Molecular Microbiology 6(3), 317–326 (1992)) in turn describe a gene library of *C. glutamicum* ATCC13032 using the cosmid pHC79 (Hohn and Collins, 1980, Gene 11, 291–298).

To prepare a gene library of *C. glutamicum* in *E. coli* it is also possible to use plasmids such as pBR322 (Bolivar, 1979, Life Sciences, 25, 807–818) or pUC9 (Vieira et al., 1982, Gene, 19:259–268). Suitable hosts are, in particular, those *E. coli* strains which are restriction- and recombination-defective, such as, for example, the strain DH5αmcr, which has been described by Grant et al. (Proceedings of the National Academy of Sciences USA, 87 (1990) 4645–4649). The long DNA fragments cloned with the aid of cosmids or other λ vectors can then in turn be subcloned and subsequently sequenced in the usual vectors which are suitable for DNA sequencing, such as is described e. g. by Sanger et al. (Proceedings of the National Academy of Sciences of the United States of America, 74:5463–5467, 1977).

The resulting DNA sequences can then be investigated with known algorithms or sequence analysis programs, such as e.g. that of Staden (Nucleic Acids Research 14, 217–232 (1986)), that of Marck (Nucleic Acids Research 16, 1829–1836 (1988)) or the GCG program of Butler (Methods of Biochemical Analysis 39, 74–97 (1998)).

The new DNA sequence of *C. glutamicum* which codes for the mikE17 gene and which, as SEQ ID No. 1, is a constituent of the present invention has been found. The amino acid sequence of the corresponding protein has furthermore been derived from the present DNA sequence by the methods described above. The resulting amino acid sequence of the mikE17 gene product is shown in SEQ ID No. 2.

Coding DNA sequences which result from SEQ ID No. 1 by the degeneracy of the genetic code are also a constituent of the invention. In the same way, DNA sequences which hybridize with SEQ ID No. 1 or parts of SEQ ID No. 1 are a constituent of the invention. Conservative amino acid exchanges, such as e.g. exchange of glycine for alanine or of aspartic acid for glutamic acid in proteins, are furthermore known among experts as "sense mutations" which do not lead to a fundamental change in the activity of the protein, i.e. are of neutral function. It is furthermore known that changes on the N and/or C terminus of a protein cannot substantially impair or can even stabilize the function thereof. Information in this context can be found by the expert, inter alia, in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in known textbooks of genetics and molecular biology. Amino acid sequences which result in a corresponding manner from SEQ ID No. 2 are also a constituent of the invention.

In the same way, DNA sequences which hybridize with SEQ ID No. 1 or parts of SEQ ID No. 1 are a constituent of the invention. Finally, DNA sequences which are prepared by the polymerase chain reaction (PCR) using primers which result from SEQ ID No. 1 are a constituent of the invention. Such oligonucleotides typically have a length of at least 15 nucleotides.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) and in Liebl et al. (International Journal of Systematic Bacteriology 41: 255–260 (1991)). The hybridization takes place under stringent conditions, that is to say only hybrids in which the probe and target sequence, i. e. the polynucleotides treated with the probe, are at least 70% identical are formed. It is known that the stringency of the hybridization, including the washing steps, is influenced or determined by varying the buffer composition, the temperature and the salt concentration. The hybridization reaction is preferably carried out under a relatively low stringency compared with the washing steps (Hybaid Hybridisation Guide, Hybaid Limited, Teddington, UK, 1996).

A 5×SSC buffer at a temperature of approx. 50° C.–68° C., for example, can be employed for the hybridization reaction. Probes can also hybridize here with polynucleotides which are less than 70% identical to the sequence of the probe. Such hybrids are less stable and are removed by washing under stringent conditions. This can be achieved, for example, by lowering the salt concentration to 2×SSC and optionally subsequently 0.5×SSC (The DIG System User's Guide for Filter Hybridisation, Boehringer Mannheim, Mannheim, Germany, 1995) a temperature of approx. 50° C.–68° C. being established. It is optionally possible to lower the salt concentration to 0.1×SSC. Polynucleotide fragments which are, for example, at least 70% or at least 80% or at least 90% to 95% identical to the sequence of the probe employed can be isolated by increasing the hybridization temperature stepwise from 50° C. to 68° C. in steps of approx. 1–2° C. Further instructions on hybridization are obtainable on the market in the form of so-called kits (e.g. DIG Easy Hyb from Roche Diagnostics GmbH, Mannheim, Germany, Catalogue No. 1603558).

Instructions for amplification of DNA sequences with the aid of the polymerase chain reaction (PCR) can be found by the expert, inter alia, in the handbook by Gait: Oligonukleotide [sic] synthesis: A Practical Approach (IRL Press, Oxford, UK, 1984) and in Newton and Graham: PCR (Spektrum Akademischer Verlag, Heidelberg, Germany, 1994).

It has been found that coryneform bacteria produce amino acids in an improved manner after attenuation of the mikE17 gene.

To achieve an attenuation, either the expression of the mikE17 gene or the regulatory properties of the enzyme protein can be reduced or eliminated. The two measures can optionally be combined.

The reduction in gene expression can take place by suitable culturing or by genetic modification (mutation) of the signal structures of gene expression. Signal structures of gene expression are, for example, repressor genes, activator genes, operators, promoters, attenuators, ribosome binding sites, the start codon and terminators. The expert can find information on this e.g. in the patent application WO 96/15246, in Boyd and Murphy (Journal of Bacteriology 170: 5949 (1988)), in Voskuil and Chambliss (Nucleic Acids Research 26: 3548 (1998), in Jensen and Hammer (Biotechnology and Bioengineering 58: 191 (1998)), in Patek et al. (Microbiology 142: 1297 (1996)), Vasicova et al. (Journal of Bacteriology 181: 6188 (1999)) and in known textbooks of genetics and molecular biology, such as e.g. the textbook by Knippers ("Molekulare Genetik [Molecular Genetics]", 6th edition, Georg Thieme Verlag, Stuttgart, Germany, 1995) or that by Winnacker ("Gene und Klone [Genes and Clones]", VCH Verlagsgesellschaft, Weinheim, Germany, 1990).

Mutations which lead to a change or reduction in the catalytic properties of enzyme proteins are known from the prior art; examples which may be mentioned are the works by Qiu and Goodman (Journal of Biological Chemistry 272: 8611–8617 (1997)), Sugimoto et al. (Bioscience Biotechnology and Biochemistry 61: 1760–1762 (1997)) and Möckel ("Die Threonindehydratase aus Corynebacterium glutamicum: Aufhebung der allosterischen Regulation und Struktur des Enzyms [Threonine dehydratase from Corynebacterium glutamicum: Cancelling the allosteric regulation and structure of the enzyme]", Reports from the Jülich Research Centre, Jül-2906, ISSN09442952, Jülich, Germany, 1994). Summarizing descriptions can be found in known textbooks of genetics and molecular biology, such as e.g. that by Hagemann ("Allgemeine Genetik [General Genetics]", Gustav Fischer Verlag, Stuttgart, 1986).

Possible mutations are transitions, transversions, insertions and deletions. Depending on the effect of the amino acid exchange on the enzyme activity, "missense mutations" or "nonsense mutations" are referred to. Insertions or deletions of at least one base pair (bp) in a gene lead to frame shift mutations, as a consequence of which incorrect amino acids are incorporated or translation is interrupted prematurely. Deletions of several codons typically lead to a complete loss of the enzyme activity. Instructions on generation of such mutations are prior art and can be found in known textbooks of genetics and molecular biology, such as e.g. the textbook by Knippers ("Molekulare Genetik [Molecular Genetics]", 6th edition, Georg Thieme Verlag, Stuttgart, Germany, 1995), that by Winnacker ("Gene und Klone [Genes and Clones]", VCH Verlagsgesellschaft, Weinheim, Germany, 1990) or that by Hagemann ("Allgemeine Genetik [General Genetics]", Gustav Fischer Verlag, Stuttgart, 1986).

A common method of mutating genes of C. glutamicum is the method of "gene disruption" and "gene replacement" described by Schwarzer and Pühler (Bio/Technology 9, 84–87 (1991)).

In the method of gene disruption a central part of the coding region of the gene of interest is cloned in a plasmid vector which can replicate in a host (typically E. coli), but not in C. glutamicum. Possible vectors are, for example, pSUP301 (Simon et al., Bio/Technology 1, 784–791 (1983)), pK18mob or pK19mob (Schäfer et al., Gene 145, 69–73 (1994)), pK18mobsacB or pK19mobsacB (Jäger et al., Journal of Bacteriology 174: 5462–65 (1992)), pGEM-T (Promega corporation, Madison, Wis., USA), pCR2.1-TOPO (Shuman (1994). Journal of Biological Chemistry 269:32678–84; U.S. Pat. No. 5,487,993), pCR®Blunt (Invitrogen, Groningen, The Netherlands; Bernard et al., Journal of Molecular Biology, 234: 534–541 (1993)) or pEM1 (Schrumpf et al, 1991, Journal of Bacteriology 173:4510–4516). The plasmid vector which contains the central part of the coding region of the gene is then transferred into the desired strain of C. glutamicum by conjugation or transformation. The method of conjugation is described, for example, by Schäfer et al. (Applied and Environmental Microbiology 60, 756–759 (1994)). Methods for transformation are described, for example, by Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a "cross-over" event, the coding region of the gene in question is interrupted by the vector sequence and two incomplete alleles are obtained, one lacking the 3' end and one lacking the 5' end. This method has been used, for example, by Fitzpatrick et al. (Applied Microbiology and Biotechnology 42, 575–580 (1994)) to eliminate the recA gene of *C. glutamicum*.

In the method of "gene replacement", a mutation, such as e.g. a deletion, insertion or base exchange, is established in vitro in the gene of interest. The allele prepared is in turn cloned in a vector which is not replicative for *C. glutamicum* and this is then transferred into the desired host of *C. glutamicum* by transformation or conjugation. After homologous recombination by means of a first "cross-over" event which effects integration and a suitable second "cross-over" event which effects excision in the target gene or in the target sequence, the incorporation of the mutation or of the allele is achieved. This method was used, for example, by Peters-Wendisch et al. (Microbiology 144, 915–927 (1998)) to eliminate the pyc gene of *C. glutamicum* by a deletion.

A deletion, insertion or a base exchange can be incorporated into the mikE17 gene in this manner.

In addition, it may be advantageous for the production of L-amino acids to enhance, in particular over-express, one or more enzymes of the particular biosynthesis pathway, of glycolysis, of anaplerosis, of the citric acid cycle, of the pentose phosphate cycle, of amino acid export and optionally regulatory proteins, in addition to the attenuation of the mikE17 gene.

The term "enhancement" in this connection describes the increase in the intracellular activity of one or more enzymes (proteins) in a microorganism which are coded by the corresponding DNA, for example by increasing the number of copies of the gene or genes, using a potent promoter or using a gene or allele which codes for a corresponding enzyme (protein) having a high activity, and optionally combining these measures.

Thus, for the preparation of L-amino acids, in addition to attenuation of the mikE17 gene, at the same time one or more of the genes chosen from the group consisting of the dapA gene which codes for dihydrodipicolinate synthase (EP-B 0 197 335), the gap gene which codes for glyceraldehyde 3-phosphate dehydrogenase (Eikmanns (1992), Journal of Bacteriology 174:6076–6086), the tpi gene which codes for triose phosphate isomerase (Eikmanns (1992), Journal of Bacteriology 174:6076–6086), the pgk gene which codes for 3-phosphoglycerate kinase (Eikmanns (1992), Journal of Bacteriology 174:6076–6086), the zwf gene which codes for glucose 6-phosphate dehydrogenase (JP-A-09224661), the pyc gene which codes for pyruvate carboxylase (DE-A-198 31 609), the mqo gene which codes for malate-quinone oxidoreductase (Molenaar et al., European Journal of Biochemistry 254, 395–403 (1998)), the lysC gene which codes for a feed-back resistant aspartate kinase (Accession No.P26512; EP-B-0387527; EP-A-0699759; WO 00/63388), the lysE gene which codes for lysine export (DE-A-195 48 222), the hom gene which codes for homoserine dehydrogenase (EP-A 0131171), the ilvA gene which codes for threonine dehydratase (Möckel et al., Journal of Bacteriology (1992) 8065–8072)) or the ilvA(Fbr) allele which codes for a "feed back resistant" threonine dehydratase (Möckel et al., (1994) Molecular Microbiology 13: 833–842), the ilvBN gene which codes for acetohydroxy-acid synthase (EP-B 0356739), the ilvD gene which codes for dihydroxy-acid dehydratase (Sahm and Eggeling (1999) Applied and Environmental Microbiology 65: 1973–1979), the zwa1 gene which codes for the Zwa1 protein (DE: 19959328.0, DSM 13115)

can be enhanced, in particular over-expressed.

It may furthermore be advantageous for the production of amino acids, in addition to attenuation of the mikE17 gene, at the same time for one or more of the genes chosen from the group consisting of the pck gene which codes for phosphoenol pyruvate carboxykinase (DE 199 50 409.1, DSM 13047), the pgi gene which codes for glucose 6-phosphate isomerase (U.S. Ser. No. 09/396,478, DSM 12969), the poxB gene which codes for pyruvate oxidase (DE:1995 1975.7, DSM 13114), the zwa2 gene which codes for the Zwa2 protein (DE: 19959327.2, DSM 13113)

to be attenuated, in particular for the expression thereof to be reduced, optionally attenuated.

In addition to attenuation of the mikE17 gene it may furthermore be advantageous for the production of amino acids to eliminate undesirable side reactions (Nakayama: "Breeding of Amino Acid Producing Microorganisms", in: Overproduction of Microbial Products, Krumphanzl, Sikyta, Vanek (eds.), Academic Press, London, UK, 1982).

The invention also provides the microorganisms prepared according to the invention, and these can be cultured continuously or discontinuously in the batch process (batch culture) or in the fed batch (feed process) or repeated fed batch process (repetitive feed process) for the purpose of production of L-amino acids. A summary of known culture methods is described in the textbook by Chmiel (Bioprozesstechnik 1. Einführung in die Bioverfahrenstechnik [Bioprocess Technology 1. Introduction to Bioprocess Technology (Gustav Fischer Verlag, Stuttgart, 1991)) or in the textbook by Storhas (Bioreaktoren und periphere Einrichtungen [Bioreactors and Peripheral Equipment] (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981).

Sugars and carbohydrates, such as e.g. glucose, sucrose, lactose, fructose, maltose, molasses, starch and cellulose, oils and fats, such as, for example, soya oil, sunflower oil, groundnut oil and coconut fat, fatty acids, such as, for example, palmitic acid, stearic acid and linoleic acid, alcohols, such as, for example, glycerol and ethanol, and organic acids, such as, for example, acetic acid, can be used as the source of carbon. These substances can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. The culture medium must furthermore comprise salts of metals, such as, for example, magnesium sulfate or iron sulfate, which are necessary for growth. Finally, essential growth substances, such as amino acids and vitamins, can be employed in addition to the abovementioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as, for example, fatty acid polyglycol esters, can be employed to control the development of foam. Suitable substances having a selective action, such as, for example, antibiotics, can be added to the medium to maintain the stability of plasmids. To maintain aerobic conditions, oxygen or oxygen-containing gas mixtures, such as, for example, air, are introduced into the culture. The temperature of the culture is usually 20° C. to 45° C., and preferably 25° C. to 40° C. Culturing is continued until a maximum of the desired product has formed. This target is usually reached within 10 hours to 160 hours.

Methods for the determination of L-amino acids are known from the prior art. The analysis can thus be carried out, for example, as described by Spackman et al. (Analytical Chemistry, 30, (1958), 1190) by anion exchange chromatography with subsequent ninhydrin derivatization, or it can be carried out by reversed phase HPLC, for example as described by Lindroth et al. (Analytical Chemistry (1979) 51: 1167–1174).

The process according to the invention is used for fermentative preparation of amino acids.

The following microorganism was deposited on 06.03.01 as a pure culture at the Deutsche Sammlung für Mikrorganismen [sic] und Zellkulturen (DSMZ=German Collection of Microorganisms and Cell Cultures, Braunschweig, Germany) in accordance with the Budapest Treaty:

*Escherichia coli* top10/pCR2.1mikE17int as DSM 14143.

The present invention is explained in more detail in the following with the aid of embodiment examples.

The isolation of plasmid DNA from *Escherichia coli* and all techniques of restriction, Klenow and alkaline phosphatase treatment were carried out by the method of Sambrook et al. (Molecular Cloning. A Laboratory Manual, 1989, Cold Spring Harbour [sic] Laboratory Press, Cold Spring Harbor, N.Y., USA). Methods for transformation of *Escherichia coli* are also described in this handbook.

The composition of the usual nutrient media, such as LB or TY medium, can also be found in the handbook by Sambrook et al.

EXAMPLE 1

Preparation of a Genomic Cosmid Gene Library from *C. glutamicum* ATCC 13032

Chromosomal DNA from *C. glutamicum* ATCC 13032 was isolated as described by Tauch et al. (1995, Plasmid 33:168–179) and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Molecular Biochemicals, Mannheim, Germany, Product Description SAP, Code no. 1758250). The DNA of the cosmid vector SuperCos1 (Wahl et al. (1987), Proceedings of the National Academy of Sciences, USA 84:2160–2164), obtained from Stratagene (La Jolla, USA, Product Description SuperCos1 Cosmid Vector Kit, Code no. 251301) was cleaved with the restriction enzyme XbaI (Amersham Pharmacia, Freiburg, Germany, Product Description XbaI, Code no. 27-0948-02) and likewise dephosphorylated with shrimp alkaline phosphatase.

The cosmid DNA was then cleaved with the restriction enzyme BamHI (Amersham Pharmacia, Freiburg, Germany, Product Description BamHI, Code no. 27-0868-04). The cosmid DNA treated in this manner was mixed with the treated ATCC13032 DNA and the batch was treated with T4 DNA ligase (Amersham Pharmacia, Freiburg, Germany, Product Description T4-DNA-Ligase, Code no. 27-0870-04). The ligation mixture was then packed in phages with the aid of Gigapack II XL Packing Extract (Stratagene, La Jolla, USA, Product Description Gigapack II XL Packing Extract, Code no. 200217).

For infection of the *E. coli* strain NM554 (Raleigh et al. 1988, Nucleic Acid Res. 16:1563–1575) the cells were taken up in 10 mM $MgSO_4$ and mixed with an aliquot of the phage suspension. The infection and titering of the cosmid library were carried out as described by Sambrook et al. (1989, Molecular Cloning: A Laboratory Manual, Cold Spring Harbor), the cells being plated out on LB agar (Lennox, 1955, Virology, 1:190)+100 µg/ml ampicillin. After incubation overnight at 37° C., recombinant individual clones were selected.

EXAMPLE 2

Isolation and Sequencing of the mikE17 Gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Molecular Biochemicals, Mannheim, Germany, Product Description SAP, Product No. 1758250). After separation by gel electrophoresis, the cosmid fragments in the size range of 1500 to 2000 bp were isolated with the QiaExII Gel Extraction Kit (Product No. 20021, Qiagen, Hilden, Germany).

The DNA of the sequencing vector pZero-1, obtained from Invitrogen (Groningen, The Netherlands, Product Description Zero Background Cloning Kit, Product No. K2500-01) was cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook et al. (1989, Molecular Cloning: A Laboratory Manual, Cold Spring Harbor), the DNA mixture being incubated overnight with T4 ligase (Pharmacia Biotech, Freiburg, Germany). This ligation mixture was then electroporated (Tauch et al. 1994, FEMS Microbiol. Letters, 123:343–7) into the *E. coli* strain DH5αmcr (Grant, 1990, Proceedings of the National Academy of Sciences, U.S.A., 87:4645–4649). Letters, 123:343–7) and plated out on LB agar (Lennox, 1955, Virology, 1:190) with 50 µg/ml zeocin.

The plasmid preparation of the recombinant clones was carried out with Biorobot 9600 (Product No. 900200, Qiagen, Hilden, Germany). The sequencing was carried out by the dideoxy chain termination method of Sanger et al. (1977, Proceedings of the National Academies of Sciences, U.S.A., 74:5463–5467) with modifications according to Zimmermann et al. (1990, Nucleic Acids Research, 18:1067). The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217–231) version 97-0. The individual sequences of the pZeroI derivatives were assembled to a continuous contig. The computer-assisted coding region analysis [sic] were prepared with the XNIP program (Staden, 1986, Nucleic Acids Research, 14:217–231). Further analyses were carried out with the "BLAST search program" (Altschul et al., 1997, Nucleic Acids Research, 25:3389–3402) against the non-redundant databank of the "National Center for Biotechnology Information" (NCBI, Bethesda, Md., USA).

The resulting nucleotide sequence is shown in SEQ ID No. 1. Analysis of the nucleotide sequence showed an open reading frame of 1425 bp, which was called the mikE17 gene. The mikE17 gene codes for a polypeptide of 474 amino acids.

EXAMPLE 3

Preparation of an Integration Vector for Integration Mutagenesis of the mikE17 Gene From the strain ATCC 13032, chromosomal DNA was isolated by the method of Eikmanns et al. (Microbiology 140: 1817–1828 (1994)). On the basis of the sequence of the mikE17 gene known for *C. glutamicum* from example 2, the following oligonucleotides were chosen for the polymerase chain reaction (see SEQ ID No. 3 and SEQ ID No. 4):

```
mikE17-int1:
5' AAT GGA TCA CGA TGT CAC C 3' mikE17-int2:
5' TAG TGG GTG AAG TGG AAG C 3'
```

The primers shown were synthesized by MWG Biotech (Ebersberg, Germany) and the PCR reaction was carried out by the standard PCR method of Innis et al. (PCR protocols. A guide to methods and applications, 1990, Academic Press) with the Taq-polymerase from Boehringer Mannheim (Germany, Product Description Taq DNA polymerase, Product No. 1 146 165). With the aid of the polymerase chain reaction, the primers allow amplification of an internal fragment of the mikE17 gene 477 bp in size. The product amplified in this way was tested electrophoretically in a 0.8% agarose gel.

The amplified DNA fragment was ligated with the TOPO TA Cloning Kit from Invitrogen Corporation (Carlsbad, Calif., USA; Catalogue Number K4500-01) in the vector pCR2.1-TOPO (Mead at al. (1991) Bio/Technology 9:657–663).

Figure 1:
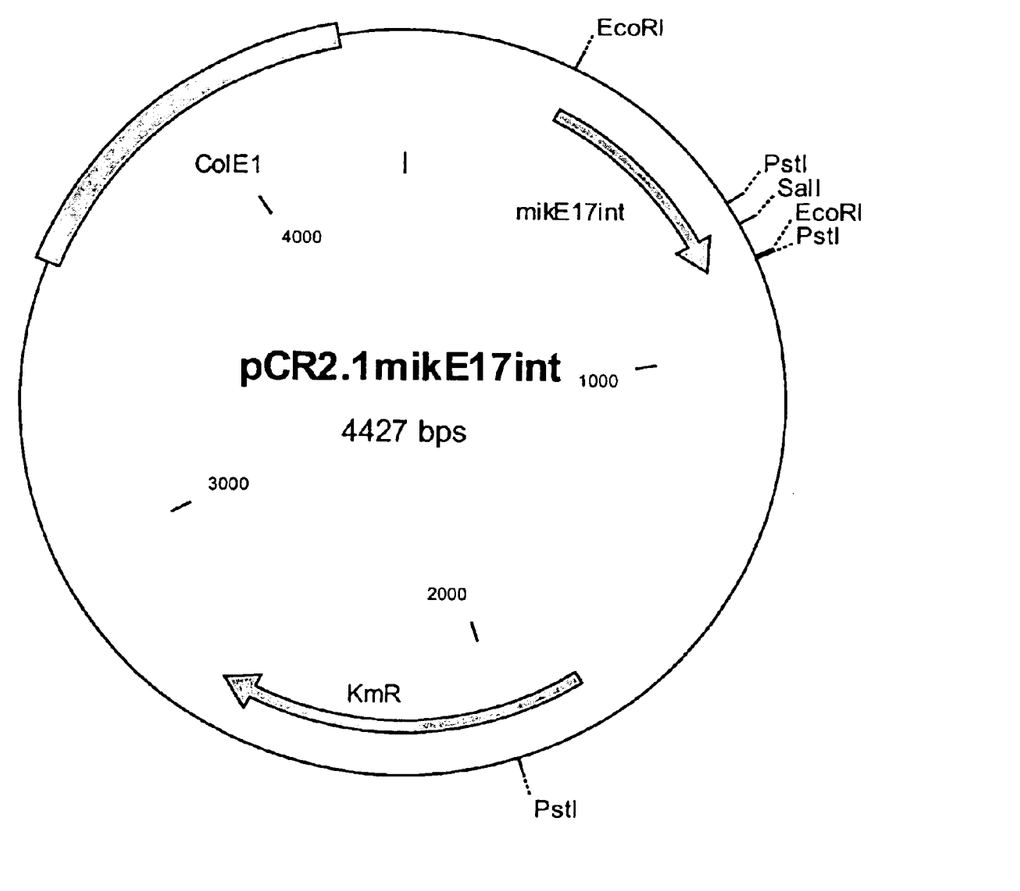
FIG. 1: Map of the plasmid pCR2.1mikE17int.

The *E. coli* strain TOP10 was then electroporated with the ligation batch (Hanahan, In: DNA cloning. A practical approach. Vol.I. IRL-Press, Oxford, Washington D.C., USA, 1985). Selection of plasmid-carrying cells was carried out by plating out the transformation batch on LB agar (Sambrook et al., Molecular cloning: a laboratory manual. $2^{nd}$ Ed. Cold Spring Harbor Laboratory Press, Cold Spring Harbor, N.Y., 1989), which had been supplemented with 50 mg/l kanamycin. Plasmid DNA was isolated from a transformant with the aid of the QIAprep Spin Miniprep Kit from Qiagen and checked by restriction with the restriction enzyme EcoRI and subsequent agarose gel electrophoresis (0.8%). The plasmid was called pCR2.1mikE17int and is shown in FIG. 1.

The following microorganism was deposited as a pure culture on 06.03.2001 at the Deutsche Sammlung für Mikroorganismen und Zellkulturen (DSMZ=German Collection of Microorganisms and Cell Cultures, Braunschweig, Germany) in accordance with the Budapest Treaty:

*Escherichia coli* Top10/pCR2.1mikE17int as DSM 14143.

EXAMPLE 4

Integration Mutagenesis of the mikE17 Gene in the Strain DSM 5715

The vector pCR2.1mikE17int mentioned in example 3 was electroporated by the electroporation method of Tauch et al.(FEMS Microbiological Letters, 123:343–347 (1994)) in *Corynebacterium glutamicum* DSM 5715. The strain DSM 5715 is an AEC-resistant lysine producer (EP-A-435 132). The vector pCR2.1mikE17int cannot replicate independently in DSM5715 and is retained in the cell only if it has integrated into the chromosome of DSM 5715. Selection of clones with pCR2.1mikE17int integrated into the chromosome was carried out by plating out the electroporation batch on LB agar (Sambrook et al., Molecular cloning: a laboratory manual. $2^{nd}$ Ed. Cold Spring Harbor Laboratory Press, Cold Spring Harbor, N.Y.), which had been supplemented with 15 mg/l kanamycin.

For detection of the integration, the mikE17int fragment was labelled with the Dig hybridization kit from Boehringer by the method of "The DIG System Users Guide for Filter Hybridization" of Boehringer Mannheim GmbH (Mannheim, Germany, 1993). Chromosomal DNA of a potential integrant was isolated by the method of Eikmanns et al. (Microbiology 140: 1817–1828 (1994)) and in each case cleaved with the restriction enzymes SalI, EcoRI and PstI. The fragments formed were separated by means of agarose gel electrophoresis and hybridized at 68° C. with the Dig hybrization [sic] kit from Boehringer. The plasmid pCR2.1mikE17int mentioned in example 3 had been inserted into the chromosome of DSM5715 within the chromosomal mikE17 gene. The strain was called DSM5715::pCR2.1mikE17int.

EXAMPLE 5

Preparation of Lysine

The *C. glutamicum* strain DSM5715::pCR2.1mikE17int obtained in example 4 was cultured in a nutrient medium suitable for the production of lysine and the lysine content in the culture supernatant was determined.

For this, the strain was first incubated on an agar plate with the corresponding antibiotic (brain-heart agar with kanamycin (25 mg/l) [sic] for 24 hours at 33° C. Starting from this agar plate culture, a preculture was seeded (10 ml medium in a 100 ml conical flask). The complete medium CgIII was used as the medium for the preculture.

| Medium Cg III | |
|---|---|
| NaCl | 2.5 g/l |
| Bacto-Peptone | 10 g/l |
| Bacto-Yeast extract | 10 g/l |
| Glucose (autoclaved separately) | 2% (w/v) |
| The pH was brought to pH 7.4 | |

Kanamycin (25 mg/l) was added to this. The preculture was incubated for 16 hours at 33° C. at 240 rpm on a shaking machine. A main culture was seeded from this preculture such that the initial OD (660 nm) of the main culture was 0.1 OD. Medium MM was used for the main culture.

| Medium MM | |
|---|---|
| CSL (corn steep liquor) | 5 g/l |
| MOPS (morpholinopropanesulfonic acid) | 20 g/l |
| Glucose (autoclaved separately) | 50 g/l |
| Salts: | |
| $(NH_4)_2SO_4$ [sic] | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterile-filtered) | 0.3 mg/l |
| Thiamine * HCl (sterile-filtered) | 0.2 mg/l |
| Leucine (sterile-filtered) | 0.1 g/l |
| $CaCO_3$ | 25 g/l |

The CSL, MOPS and the salt solution are brought to pH 7 with aqueous ammonia and autoclaved. The sterile substrate and vitamin solutions are then added, and the $CaCO_3$ autoclaved in the dry state is added.

Culturing is carried out in a 10 ml volume in a 100 ml conical flask with baffles. Kanamycin (25 mg/l) was added. Culturing was carried out at 33° C. and 80% atmospheric humidity.

After 72 hours, the OD was determined at a measurement wavelength of 660 nm with a Biomek 1000 (Beckmann Instruments GmbH, Munich). The amount of lysine formed was determined with an amino acid analyzer from Eppendorf-BioTronik (Hamburg, Germany) by ion exchange chromatography and post-column derivatization with ninhydrin detection.

The result of the experiment is shown in table 1.

TABLE 1

| Strain | OD (660) | Lysine HCl g/l |
|---|---|---|
| DSM5715 | 7.4 | 13.05 |
| DSM5715::pCR2.1mikE17int | 7.6 | 15.14 |

The abbreviations and designations used have the following meaning.

| | |
|---|---|
| KmR: | Kanamycin resistance gene |
| EcoRI: | Cleavage site of the restriction enzyme EcoRI |
| PstI: | Cleavage site of the restriction enzyme PstI |
| SalI: | Cleavage site of the restriction enzyme SalI |
| mikE17int: | Internal fragment of the mikE17 gene |
| ColE1: | Replication origin of the plasmid ColE1 |

What is claimed is:

1. An isolated polynucleotide encoding a protein with an amino acid sequence comprising the sequence as set forth in SEQ ID NO: 2.

2. An isolated polynucleotide consisting of nucleotides 252–1673 of SEQ ID NO: 1 or fragment thereof which encodes a transcription regulator protein that inhibits lysine production in a bacterial cell.

3. An isolated polynucleotide consisting of nucleotides encoding a protein consisting of the amino acid sequence of SEQ ID NO: 2.

4. An isolated polynucleotide comprising the nucleotide sequence of SEQ ID NO: 1 or its complement.

5. A vector comprising a sequence identical to that of the isolated polynucleotide of any one of claims 1–3, and 4.

6. A bacterium transformed with the vector of claim 5.

7. The bacterium of claim 6, wherein said vector is integrated into the bacterial genome and disrupts the endogenous mikE17 gene.

8. The vector pCR2.1mikE17int.

9. A bacterium transformed with the vector of claim 8.

10. The isolated polynucleotide of any one of claim 1 or 4, wherein said polynucleotide is isolated from coryneform bacterium.

11. An isolated polynucleotide which hybridizes under stringent conditions to the complement of SEQ ID NO: 1 and encodes a transcription regulator protein that inhibits lysine production in a bacterial cell, wherein said stringent conditions comprise washing in 0.5×SSC at a temperature of 68° C.

12. An isolated polynucleotide which hybridizes under stringent conditions to the complement of SEQ ID NO: 1 and encodes a transcription regulator protein that inhibits lysine production in a bacterial cell, wherein said stringent conditions comprise washing in 0.1×SSC at a temperature of 68° C.

13. The isolated polynucleotide of either claim 11 or 12, wherein said polynucleotide encodes a protein consisting of the amino acid sequence of SEQ ID NO: 2.

14. The isolated polynucleotide of any one of claims 11–13, wherein said polynucleotide is isolated from a coryneform bacterium.

15. An isolated polynucleotide consisting essentially of at least 30 consecutive nucleotides from the complement of SEQ ID NO:1 having the function of a probe in a hybridization reaction that may be used to isolate or identify a polynucleotide encoding a protein comprising the amino acid sequence of SEQ ID NO:2.

16. A vector comprising the polynucleotide of claim 15.

* * * * *